US007985877B2

(12) United States Patent
Ohtsuka et al.

(10) Patent No.: US 7,985,877 B2
(45) Date of Patent: Jul. 26, 2011

(54) CARBOXYLIC ACID COMPOUND, USE THEREOF, AND PROCESS FOR PRODUCING THE SAME

(75) Inventors: Tatsuya Ohtsuka, Settsu (JP); Yoshihiro Yamamoto, Settsu (JP); Yoshichika Kuroki, Settsu (JP); Atsushi Suzuki, Settsu (JP); Akinari Sugiyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 426 days.

(21) Appl. No.: 12/301,543

(22) PCT Filed: May 31, 2007

(86) PCT No.: PCT/JP2007/061063
§ 371 (c)(1),
(2), (4) Date: Nov. 19, 2008

(87) PCT Pub. No.: WO2007/142110
PCT Pub. Date: Dec. 13, 2007

(65) Prior Publication Data
US 2009/0156861 A1    Jun. 18, 2009

(30) Foreign Application Priority Data

Jun. 5, 2006  (JP) ................ 2006-156037
Dec. 20, 2006  (JP) ................ 2006-342327

(51) Int. Cl.
C07C 59/135 (2006.01)
C07C 41/18 (2006.01)
C07C 41/22 (2006.01)
C07C 43/12 (2006.01)
C07C 51/09 (2006.01)
C07C 51/367 (2006.01)

(52) U.S. Cl. .......... 562/605; 562/586; 568/683

(58) Field of Classification Search .......... None
See application file for complete search history.

(56) References Cited

U.S. PATENT DOCUMENTS

| 3,321,515 A | 5/1967 | Moore |
| 3,544,633 A | 12/1970 | Yodis |
| 3,683,092 A | 8/1972 | Regan |
| 3,883,665 A | 5/1975 | Croix |
| 4,250,334 A | 2/1981 | Coon |
| 5,466,879 A | 11/1995 | Cheburkov |
| 5,990,359 A | 11/1999 | Ryan |
| 6,469,219 B1 | 10/2002 | Khrimian |

FOREIGN PATENT DOCUMENTS

| EP | 0 901 999 | 3/1999 |
| JP | 61-25694 | 2/1986 |
| JP | 61-277645 | 12/1986 |
| JP | 1-203339 | 8/1989 |
| JP | 6-184025 | 7/1994 |
| JP | 11-116521 | 4/1999 |
| JP | 2002-234860 | 8/2002 |
| JP | 2002-234860 A1 | 8/2002 |
| JP | 2005-306747 A1 | 11/2005 |
| WO | WO 97/30961 A1 | 8/1997 |
| WO | 2004/065340 | 8/2004 |

OTHER PUBLICATIONS

Supplementary European Search Report dated Apr. 21, 2010 issued in European Application No. 07 74 4472 corresponding to present US application.
International Search Report for International Application No. PCT/JP2007/061063 dated Aug. 2, 2007.

*Primary Examiner* — Daniel Sullivan
*Assistant Examiner* — Yevegeny Valenrod
(74) *Attorney, Agent, or Firm* — Wenderoth, Lind & Ponack, L.L.P.

(57) ABSTRACT

The present invention provides a process for producing 1,1,1,3,3,3-hexafluoro-2-methoxypropane, wherein a novel compound, 2-methoxy-2-trifluoromethyl-3,3,3-trifluoropropionic acid or a salt thereof is decarboxylated, or wherein an olefin compound represented by chemical formula (4): $CF_2=C(CF_3)(OCH_3)$ is reacted with a fluorinating agent; and a process for producing 2-methoxy-2-trifluoromethyl-3,3,3-trifluoropropionic acid or a salt thereof by reacting a hydroxycarboxylic ester with a methylating agent and then hydrolyzing the reaction product, or hydrolyzing the hydroxycarboxylic ester and then reacting the resulting product with a methylating agent.

In accordance with the invention, 1,1,1,3,3,3-hexafluoro-2-methoxypropane, which is useful as a raw material for, for example, the anesthetic Sevoflurane, can be produced efficiently and at low cost.

15 Claims, No Drawings

CARBOXYLIC ACID COMPOUND, USE THEREOF, AND PROCESS FOR PRODUCING THE SAME

TECHNICAL FIELD

The present invention relates to a novel carboxylic acid or a salt thereof, which is useful as an intermediate of 1,1,1,3,3,3-hexafluoro-2-methoxypropane, a process for producing the same, and a process for producing 1,1,1,3,3,3-hexafluoro-2-methoxypropane.

BACKGROUND ART 1,1,1,3,3,3-Hexafluoro-2-methoxypropane, represented by the chemical formula: $(CF_3)_2CH(OCH_3)$, is a material useful as a raw material for the anesthetic Sevoflurane (see Patent Documents 1, 2, etc. listed below). The production of Sevoflurane at low cost is an important issue, and various processes have so far been contemplated.

For example, Patent Document 1 listed below discloses a process wherein 1,1,1,3,3,3-hexafluoro-2-propyl methyl ether, obtained by methylation of hexafluoroisopropanol (HFIP), is reacted with chlorine gas to give 1,1,1,3,3,3-hexafluoro-2-propyl chloromethyl ether, and then this compound is reacted with KF in an organic solvent to produce Sevoflurane; a process wherein 1,1,1,3,3,3-hexafluoro-2-propyl methyl ether is reacted with $BrF_3$; and a process wherein HFIP is reacted with hydrogen fluoride and formaldehyde.

However, the reaction in which the chloromethyl ether is fluorinated with KF has the drawback of requiring a high temperature and a prolonged reaction, and thus poses problems for implementation on an industrial scale. The process wherein the methyl ether is reacted with $BrF_3$ requires handling of the dangerous $BrF_3$, and is therefore not suitable for mass production. The process wherein HFIP is reacted with hydrogen fluoride and formaldehyde suffers from a low yield due to the formation of a polyether as a by-product.

To overcome these problems, Patent Document 3 listed below, for example, discloses a process wherein hydrogen fluoride and paraformaldehyde are reacted with HFIP in the presence of sulfuric acid. Moreover, Patent Document 2 listed below discloses a process wherein the methyl ether of HFIP is reacted with chlorine gas to produce 1,1,1,3,3,3-hexafluoro-2-propyl chloromethyl ether, which is then reacted with hydrogen fluoride and amine.

With respect to the process wherein hydrogen fluoride and paraformaldehyde are reacted with HFIP in the presence of sulfuric acid, the following inventions have further been made as processes for improving the yield.

For example, Patent Document 4 listed below discloses a process wherein a polyether compound formed as a by-product during the reaction is reacted with hydrogen fluoride and a reaction accelerator such as sulfuric acid or the like to produce Sevoflurane. Patent Document 5 listed below discloses a process wherein hydrogen fluoride and paraformaldehyde are reacted with HFIP in the presence of sulfuric acid, and the formed Sevoflurane is extracted from the mixture at equilibrium by distillation or extraction, thereby increasing the yield.

Moreover, Patent Document 6 discloses a process wherein HFIP is reacted with bis(fluoromethyl)ether in the presence of acid.

In addition to the above-described processes, a number of processes for producing Sevoflurane are known, and most of these processes use HFIP as a starting material. As a process for producing HFIP, a process wherein hexafluoroacetone or its hydrate is reduced by hydrogen in the presence of a catalyst (see Patent Documents 7, 8 listed below, etc.) is known. Among known processes for producing hexafluoroacetone, a process wherein hexafluoropropylene oxide is rearranged in the presence of a catalyst (Patent Document 9), and a process wherein hexachloroacetone is fluorinated with hydrogen fluoride (Patent Document 10) are known. The former process, however, has a problem in that the starting material, i.e., hexafluoropropylene oxide, is expensive. The latter process also has problems in that the purification processes for separating the resulting hexafluoroacetone from hydrochloric acid, for separating the byproduct chlorofluoroacetone, and the like are complicated, making the process costly.

In view of these circumstances, attempts have been made to produce hexafluoroacetone at low cost. Processes that are attracting attention, in particular, are those using, as starting materials, $(CF_3)_2CHCF_2OCH_3$ (2H-octafluoroisobutyl methyl ether; hereinafter abbreviated to "OIME") obtained by reacting methanol with octafluoroisobutene which is a by-product of hexafluoropropene that is mass-produced as a monomer for fluororesins, $(CF_3)_2C=CFOCH_3$ (heptafluoroisobutenyl methyl ether; hereinafter abbreviated to "HIME") obtained by removing HF from OIME, and the like.

Patent Document 11, for example, discloses a process for producing hexafluoroacetone hydrate, wherein HIME is reacted with oxygen under photoradiation.

Patent Document 12 discloses a process for producing hexafluoroacetone or its hydrate, wherein OIME or HIME is reacted with oxygen in the presence of an activated carbon catalyst.

Patent Document 13 discloses a process for producing hexafluoroacetone, wherein OIME is reacted with triethylamine to give hexafluoroacetone oxime, which is then hydrolyzed with acid.

Patent Document 14 discloses a process for producing hexafluoroacetone hydrate, wherein $(CF_3)_2C(OH)CO_2CH_3$ (methyl 3,3,3-trifluoro-2-trifluoromethyl-2-hydroxypropionate; hereinafter abbreviated to "MTTHP") is hydrolyzed and then decarboxylated by reacting the hydrolysis product with a halogenating agent.

The process utilizing the photo-oxidation of HIME, however, has problems in that it is difficult to industrially perform photoradiation, and that the yield is low. The oxidation process using an activated carbon catalyst has problems such as inability to perform a long-term operation due to significant degradation of the catalyst, a low selectivity of hexafluoroacetone, and the like. The process wherein OIME is reacted with triethylamine to give an oxime has a problem in that triethylamine, which is an auxiliary starting material, is expensive. The process wherein MTTHP is hydrolyzed and then decarboxylated by halogenation uses an inexpensive auxiliary starting material and has a high yield, but it has the drawback of requiring a large number of steps.

Processes for producing HFIP at low cost without using the intermediate hexafluoroacetone have been contemplated as follows.

For example, Patent Document 15 discloses a process for producing HFIP, comprising synthesizing MTTHP by oxidation of HIME, hydrolyzing the resulting MTTHP, and decarboxylating the hydrolysis product in the presence of a protonic solvent. As a result of re-examination performed by the inventors, however, this process was found to have a low yield because of the formation of $CF_3(HCF_2)C=O$ (pentafluoroacetone) as a by-product during decarboxylation.

As described above, although the production of hexafluoroacetone or HFIP at low cost is an important issue, satisfactory results have yet to be obtained.

Accordingly, in order to produce Sevoflurane at low cost, there is a strong desire for the development of a process for producing hexafluoroacetone or HFIP at low cost, or the development of a process for producing Sevoflurane without using these intermediates.

Patent Document 1: U.S. Pat. No. 3,683,092
Patent Document 2: Japanese Unexamined Patent Publication No. 11-116521
Patent Document 3: U.S. Pat. No. 4,250,334
Patent Document 4: WO 97/30961
Patent Document 5: U.S. Pat. No. 6,469,219
Patent Document 6: U.S. Pat. No. 5,990,359
Patent Document 7: Japanese Examined Patent Publication No. 61-25694
Patent Document 8: Japanese Unexamined Patent Publication No. 6-184025
Patent Document 9: U.S. Pat. No. 3,321,515
Patent Document 10: U.S. Pat. No. 3,544,633
Patent Document 11: Japanese Unexamined Patent Publication No. 61-277645
Patent Document 12: Japanese Unexamined Patent Publication No. 1-203339
Patent Document 13: U.S. Pat. No. 5,466,879
Patent Document 14: Japanese Unexamined Patent Publication No. 2005-306747
Patent Document 15: Japanese Unexamined Patent Publication 2002-234860

DISCLOSURE OF THE INVENTION

Problems to be Solved by the Invention

The present invention was made in view of the above-described current status of the prior art. A primary object of the invention is to provide a process capable of efficient and low-cost production of 1,1,1,3,3,3-hexafluoro-2-methoxypropane, represented by the general formula: $(CF_3)_2CH(OCH_3)$, which is useful as a raw material for the anesthetic Sevoflurane, and a novel compound useful in the production of 1,1,1,3,3,3-hexafluoro-2-methoxypropane.

Means for Solving the Problems

The inventors have engaged in extensive research to achieve the above-mentioned object. Consequently, the inventors found that a novel carboxylic acid or a salt thereof can be produced in a high yield according to a process using a known compound, 3,3,3-trifluoro-2-trifluoromethyl-2-hydroxypropionic ester, as a starting material, wherein the hydroxy group thereof is reacted with a methylating agent and then the resulting product is hydrolyzed, or according to a process wherein the above-mentioned starting material is hydrolyzed and then reacted with a methylating agent. The inventors also found that, by decarboxylating the novel carboxylic acid or the salt thereof by heat treatment, the target 1,1,1,3,3,3-hexafluoro-2-methoxypropane can be produced in a good yield, using a relatively simple process. Furthermore, the inventors found that the target 1,1,1,3,3,3-hexafluoro-2-methoxypropane can also be obtained by reacting a specific fluorinating agent with an olefin formed during the decarboxylation reaction as a by-product. The present invention was accomplished based on these findings.

More specifically, the invention provides a novel carboxylic acid compound and a production process therefor, as well as a process for producing 1,1,1,3,3,3-hexafluoro-2-methoxypropane from the carboxylic acid compound, as summarized below.

Item 1. 2-Methoxy-2-trifluoromethyl-3,3,3-trifluoropropionic acid represented by chemical formula (1): $(CF_3)_2C(OCH_3)COOH$ or a salt thereof.

Item 2. A process for producing 1,1,1,3,3,3-hexafluoro-2-methoxypropane represented by chemical formula (2): $(CF_3)_2CH(OCH_3)$, comprising decarboxylating 2-methoxy-2-trifluoromethyl-3,3,3-trifluoropropionic acid represented by chemical formula (1): $(CF_3)_2C(OCH_3)COOH$ or a salt thereof.

Item 3. The process for producing 1,1,1,3,3,3-hexafluoro-2-methoxypropane according to Item 2, wherein the decarboxylation reaction is performed in the presence of an organic solvent.

Item 4. The process for producing 1,1,1,3,3,3-hexafluoro-2-methoxypropane according to Item 2, wherein the decarboxylation reaction is performed in the presence of an organic solvent and an equimolar or excess amount of water relative to the 2-methoxy-2-trifluoromethyl-3,3,3-trifluoropropionic acid represented by chemical formula (1): $(CF_3)_2C(OCH_3)COOH$ or a salt thereof.

Item 5. The process for producing 1,1,1,3,3,3-hexafluoro-2-methoxypropane according to Item 3 or 4, wherein the organic solvent is at least one solvent selected from the group consisting of amide solvents, nitrile solvents, ketone solvents, sulfone solvents, and sulfoxide solvents.

Item 6. The process for producing 1,1,1,3,3,3-hexafluoro-2-methoxypropane according to any one of Items 2 to 5, wherein the decarboxylation reaction is performed further in the presence of one or more fluorinating agents represented by the chemical formula: $MF \cdot (HF)_n$, wherein M is H, Na, K, or Cs, and n is an integer from 0 to 2.

Item 7. A process for producing 1,1,1,3,3,3-hexafluoro-2-methoxypropane represented by chemical formula (2): $(CF_3)_2CH(OCH_3)$, comprising reacting 1,1,1,3,3,3-hexafluoro-2-methoxy-2-propene represented by chemical formula (4): $CF_2=C(CF_3)(OCH_3)$ with one or more fluorinating agents represented by the chemical formula: $MF \cdot (HF)_n$, wherein M is H, Na, K, or Cs, and n is an integer from 0 to 2.

Item 8. A process for producing 2-methoxy-2-trifluoromethyl-3,3,3-trifluoropropionic acid represented by chemical formula (1): $(CF_3)_2C(OCH_3)COOH$ or a salt thereof, comprising reacting a methylating agent with a hydroxycarboxylic ester represented by general formula (3):

$(CF_3)_2C(OH)COOR$, wherein R is a hydrocarbon group, and may contain at least one atom selected from the group consisting of halogen, oxygen, nitrogen, and sulfur atoms, and subsequently hydrolyzing the resulting reaction product.

Item 9. The process according to Item 8, wherein the methylating agent is at least one compound selected from the group consisting of dimethyl sulfate, chloromethane, bromomethane, and iodomethane.

Item 10. A process for producing 2-methoxy-2-trifluoromethyl-3,3,3-trifluoropropionic acid represented by chemical formula (1): $(CF_3)_2C(OCH_3)COOH$ or a salt thereof, comprising hydrolyzing a hydroxycarboxylic ester represented by general formula (3):

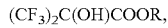
$(CF_3)_2C(OH)COOR$, wherein R is a hydrocarbon group, and may contain at least one atom selected from the group consisting of halogen, oxygen, nitrogen, and sulfur atoms, to produce 1,1,1-trifluoro-2-trifluoromethyl-2-hydroxypropionic acid represented by the chemical formula: $(CF_3)_2C(OH)CO_2H$ or a salt thereof, and subsequently reacting the resulting product with a methylating agent.

Item 11. The process according to Item 10, wherein the methylating agent is at least one compound selected from the group consisting of dimethyl sulfate, chloromethane, bromomethane, and iodomethane.

The novel carboxylic acid compound useful as an intermediate of 1,1,1,3,3,3-hexafluoro-2-methoxypropane and the production process therefor are described first below, and subsequently the process for producing 1,1,1,3,3,3-hexafluoro-2-methoxypropane from the carboxylic acid compound is described.

Novel Carboxylic Acid Compound and Production Process Therefor

The novel carboxylic acid or salt thereof, useful as an intermediate of 1,1,1,3,3,3-hexafluoro-2-methoxypropane, can be produced using, as a starting material, a hydroxycarboxylic ester represented by general formula (3): $(CF_3)_2C(OH)COOR$, wherein R is a hydrocarbon group, and may contain at least one atom selected from the group consisting of halogen, oxygen, nitrogen, and sulfur atoms. The compound of general formula (3) is known and described in, for example, Japanese Unexamined Patent Publication No. 2002-234860.

In general formula (3) above, examples of hydrocarbon groups represented by R include $C_1$-$C_{10}$ alkyl, aryl, aralkyl, and the like. Preferable as the alkyl are methyl, ethyl, isopropyl, t-butyl, and hexyl. Preferable as the aryl are phenyl, naphthyl, pyridyl, chlorophenyl, and the like. Preferable as the aralkyl are benzyl, phenethyl, and the like. Among these examples, methyl is particularly preferable because of production at low cost.

(i) In accordance with a first process of the invention, 2-methoxy-2-trifluoromethyl-3,3,3-trifluoropropionic acid represented by chemical formula (1): $(CF_3)_2C(OCH_3)COOH$ or a salt thereof can be produced by reacting the hydroxycarboxylic ester represented by general formula (3) above with a methylating agent, and subsequently hydrolyzing the reaction product.

2-Methoxy-2-trifluoromethyl-3,3,3-trifluoropropionic acid represented by chemical formula (1) above or a salt thereof is a novel compound not disclosed by any literature, and is useful as an intermediate of 1,1,1,3,3,3-hexafluoro-2-methoxypropane.

Examples of the salts of the carboxylic acid represented by chemical formula (1) above include various metal salts, ammonium salts, and the like. More specifically, salts of monovalent cations such as $Li^+$, $Na^+$, $K^+$, $NH_4^+$, $H^+$, $Ag^+$, and the like; salts of divalent cations such as $1/2Mg^{2+}$, $1/2Ca^{2+}$, $1/2Ba^{2+}$, $1/2Pb^{2+}$, $1/2Cu^{2+}$, and the like; salts of trivalent cations such as $1/3Al^{3+}$, $1/3Fe^{3+}$, and the like can be mentioned. Among these salts, salts of $Li^+$, $Na^+$, $K^+$, $1/2Mg^{2+}$, $1/2Ca^{2+}$, and the like are particularly preferable because they can be easily obtained by hydrolyzing esters.

The hydroxycarboxylic ester represented by general formula (3) can be methylated by reacting the hydroxycarboxylic ester with a methylating agent in the presence of an alkaline compound. This reaction can be performed either in the presence or absence of a solvent.

Compounds known as general methylating agents for alcohols are usable as the methylating agent. Specific examples of methylating agents include halogenated methanes such as chloromethane ($CH_3Cl$), bromomethane ($CH_3Br$), iodomethane ($CH_3I$), and the like, as well as dimethyl sulfate, dimethyl carbonate, and the like.

The amount of methylating agent may be from about 0.2 to about 10 equivalents, preferably about 1 to about 2 equivalents, and more preferably about 1 to 1.5 equivalents, per equivalent of the hydroxycarboxylic ester represented by general formula (3).

During the methylation, it is necessary to add an alkaline compound to convert the hydroxy group into an alkoxide. Those that can be suitably used as the alkaline compound include carbonates, hydrogen carbonates, hydroxides, oxides, and the like of alkali metals (such as Li, K, Na, and the like) or alkaline earth metals (such as Mg, Ca, Ba, and the like). The amount of alkaline compound may be from about 0.2 to about 10 equivalents, preferably about 1 to about 2 equivalents, and more preferably about 1 to about 1.5 equivalents, per equivalent of the hydroxycarboxylic ester represented by general formula (3).

While the reaction temperature depends on the type of methylating agent, it may typically be from about 0 to about 200° C., preferably about 20 to about 120° C., and more preferably about 30 to about 100° C. The reaction time may typically be from about 10 minutes to about 24 hours, and preferably about 1 to about 10 hours.

The methylated ester compound thus obtained in the step described above can be hydrolyzed by reacting it with water in the presence of an alkaline compound or an acid catalyst to produce 2-methoxy-2-trifluoromethyl-3,3,3-trifluoropropionic acid represented by chemical formula (1) or its salt. Examples of alkaline compounds that can be suitably used include hydroxides, oxides, carbonates, and the like of alkali metals (such as Li, K, Na, and the like) or alkaline earth metals (such as Mg, Ca, Ba, and the like). Examples of acid catalysts that can be suitably used include sulfuric acid, hydrochloric acid, nitric acid, phosphoric acid, and the like. The amount of alkaline compound may be from about 0.2 to about 10 equivalents, preferably about 1 to about 2 equivalents, and more preferably about 1 to about 1.5 equivalents, per equivalent of the methylated ester compound. The amount of acid catalyst may be from about 0.01 to about 10 equivalents, and preferably about 0.1 to about 1 equivalent, per equivalent of the methylated ester compound.

While the reaction temperature cannot be generalized because it depends on the type of the alkaline compound or acid catalyst, it may typically be from about 0 to about 100° C., preferably about 20 to about 80° C., and more preferably about 30 to about 60° C.

The reaction time may typically be from about 10 minutes to about 24 hours, and preferably about 1 to about 10 hours.

2-Methoxy-2-trifluoromethyl-3,3,3-trifluoropropionic acid represented by chemical formula (1) above can be produced by hydrolysis in the presence of an acid catalyst. Among the salts of the carboxylic acid, salts of Li, K, Na, Mg, Ca, and the like can be produced by hydrolysis in the presence of an alkaline compound containing any of these metal components. Salts of other metal atoms, ammonium salts, and the like can be produced from the acid represented by general formula (1) or its salt via a salt-exchange reaction or a salt-forming reaction.

(ii) In accordance with a second process of the invention, the carboxylic acid represented by general formula (1): $(CF_3)_2C(OCH_3)COOH$ or its salt can also be produced by hydrolyzing the hydroxycarboxylic ester represented by general formula (3) above to produce 1,1,1-trifluoro-2-trifluoromethyl-2-hydroxypropionic acid represented by the chemical formula: $(CF_3)_2C(OH)CO_2H$ or its salt, and subsequently reacting the resulting product with a methylating agent.

Hydrolysis of the hydroxycarboxylic ester represented by general formula (3) can be performed in the same manner as the hydrolysis of the methylated ester compound in the above-described first process. Salts of Li, K, Na, Mg, Ca, and the like can be produced by hydrolysis in the presence of an alkaline compound containing any of these metal components. Salts of other metal atoms, ammonium salts, and the like can be produced by a salt-exchange reaction or a salt-forming reaction from 1,1,1-trifluoro-2-trifluoromethyl-2-hydroxypropionic acid represented by the chemical formula: $(CF_3)_2C(OH)CO_2H$ or its salt obtained by hydrolysis.

1,1,1-Trifluoro-2-trifluoromethyl-2-hydroxypropionic acid or its salt is subsequently reacted with a methylating agent to produce the carboxylic acid represented by general formula (1): $(CF_3)_2C(OCH_3)COOH$ or a salt thereof.

The reaction with a methylating agent can be performed under the same conditions as employed in the reaction of the hydroxycarboxylic ester with a methylating agent in the above-described first process.

Process for Producing 1,1,1,3,3,3-Hexafluoro-2-methoxypropane (i) Decarboxylation Reaction:

In the present invention, 1,1,1,3,3,3-hexafluoro-2-methoxypropane represented by chemical formula (2): $(CF_3)_2CH(OCH_3)$ can be produced via the decarboxylation reaction by heating 2-methoxy-2-trifluoromethyl-3,3,3-trifluoropropionic acid represented by chemical formula (1): $(CF_3)_2C(OCH_3)COOH$ or its salt obtained according to the above-described first or second process.

The decarboxylation reaction can be performed by heating the carboxylic acid represented by chemical formula (1) or its salt. When the carboxylic acid represented by chemical formula (1) is used, it may be heated in a solid state; however, when a salt of the carboxylic acid represented by chemical formula (1) is used, it is necessary to perform the decarboxylation reaction in the presence of water. In this case, it is necessary to use an equimolar or excess amount of water relative to the salt of the carboxylic acid represented by chemical formula (1). Alternatively, the carboxylic acid or its salt may be heated in aqueous solution form, using water as a solvent. When the carboxylic acid or its salt is subjected to the decarboxylation reaction in aqueous solution form, the concentration of the carboxylic acid represented by chemical formula (1) or its salt is not limited; however, the concentration may typically be from about 0.1 to about 60 mass %, and the aqueous solution may contain the carboxylic acid or its salt in an amount that exceeds the saturated concentration. Especially at a high concentration, the reaction can be efficiently performed.

The yield of the target material, 1,1,1,3,3,3-hexafluoro-2-methoxypropane represented by general formula (2): $(CF_3)_2CH(OCH_3)$, can be enhanced by performing the above-described decarboxylation reaction in the presence of an organic solvent to thereby reduce the production of an olefin compound represented by chemical formula (4): $CF_2=C(CF_3)(OCH_3)$, which is a by-product formed during the decarboxylation reaction, a hydrolysis product represented by chemical formula (5): $CF_3CH(OCH_3)(COONa)$, and the like.

Solvents with a high dielectric constant are preferably used as organic solvents, and examples of such organic solvents that can be suitably used include amide solvents such as N,N-dimethylformamide, N-methylpyrrolidone, N,N-dimethylacetamide, and the like; nitrile solvents such as acetonitrile, propionitrile, and the like; ketone solvents such as acetone, methyl ethyl ketone, methyl isobutyl ketone and the like; sulfoxide solvents such as dimethyl sulfoxide and the like; and sulfone solvents such as sulfolane and the like. These organic solvents can be used alone or in combination.

While the concentration of the carboxylic acid represented by chemical formula (1): $(CF_3)_2C(OCH_3)COOH$ or its salt in an organic solvent is not limited, it may typically be from about 0.01 to about 1 mol/L.

When the decarboxylation reaction is performed in an organic solvent, water may be added, and the reaction may be performed in a mixed solvent. In the case of a mixed solvent, the ratio of water to organic solvent is not limited, but may, for example, be from about 100:1 to about 1:100 by volume.

Especially when the decarboxylation reaction of a salt of the carboxylic acid represented by chemical formula (1): $(CF_3)_2C(OCH_3)COOH$ is performed in an organic solvent, it is necessary to add an equimolar or excess amount of water relative to the salt, as described above. If water is not added, the selectivity of the olefin compound increases to reduce the selectivity of the target material. Water is preferably added in an amount of from about 1 to about 30 mol, and more preferably from about 5 to about 15 mol, per mol of the carboxylic acid salt.

The decarboxylation reaction may be performed after isolating the carboxylic acid represented by chemical formula (1) or its salt, or the decarboxylation reaction may be performed directly without isolating the carboxylic acid represented by chemical formula (1) or its salt. When the carboxylic acid represented by chemical formula (1) or its salt is not isolated, one-pot decarboxylation can be performed from the starting hydroxycarboxylic ester of general formula (3).

However, when one-pot decarboxylation reaction is performed, a mixture of an alcohol represented by ROH, which is a hydrolysis product, and the target 1,1,1,3,3,3-hexafluoro-2-methoxypropane represented by chemical formula (2) is produced. Although the alcohol represented by ROH can be separated from the target fluoroalkyl ether by washing with water, production of wastewater containing the alcohol increases costs. For this reason, the decarboxylation reaction by heating is preferably performed after separating the alcohol represented by ROH from the carboxylic acid represented by chemical formula (1) or its salt by distillation.

The reaction temperature during the decarboxylation reaction may typically be from about 60 to about 200° C., preferably from about 80 to about 150° C., and more preferably from about 80 to about 120° C. A reaction temperature that is too low is not preferable because the rate of reaction will become slow, whereas a reaction temperature that is too high is also not preferable because the amount of unwanted by-products will increase.

To increase the rate of reaction, adding at least one component selected from the group consisting of (polyethylene glycols and alkyl ethers thereof is effective. Examples of preferable additives include ethylene glycol, diethylene glycol, triethylene glycol, tetraethyleneglycol, monoalkyl ethers thereof such as monomethyl ethers, monoethyl ethers and the like, and dialkyl ethers thereof such as dimethyl ethers, diethyl ethers, and the like.

The amount of the (polyethylene glycols and alkyl ethers thereof is from about 0 to about 100 parts by weight, and preferably from about 0.001 to about 10 parts by weight, per part by weight of the carboxylic acid represented by chemical formula (1) or its salt. If these additives are not used, the reaction time will be long, but the reaction will proceed without any problems.

The reaction time depends upon the reaction temperature and the amount of additives. When the additives are used, a sufficient reaction time is from about 2 to about 5 hours at 80° C.

In the above-described decarboxylation reaction, one or more fluorinating agents represented by the chemical formula: $MF \cdot (HF)_n$, wherein M is H, Na, K, or Cs, and n is an integer from 0 to 2, can be added to further enhance the yield of the target 1,1,1,3,3,3-hexafluoro-2-methoxypropane represented by chemical formula (2).

Specific examples of fluorinating agents represented by the chemical formula: $MF \cdot (HF)_n$ include hydrogen fluoride, sodium fluoride, potassium fluoride, cesium fluoride, acidic potassium fluoride ($KHF_2$), acidic sodium fluoride ($NaHF_2$), and the like. These fluorinating agents can be used alone or in combination.

The amount of the fluorinating agent represented by the chemical formula: $MF \cdot (HF)_n$ is preferably from about 0.01 to about 3 equivalents, and more preferably about 0.5 to about 1.2 equivalents, per equivalent of the carboxylic acid represented by chemical formula (1) or its salts.

The fluorinating agent can be used in both methods wherein the decarboxylation reaction is performed in a solid state, and wherein the decarboxylation reaction is performed in a solution. When, however, the fluorinating agent is sodium fluoride, potassium fluoride, or cesium fluoride, the reaction must be performed in the presence of about an equimolar or excess amount of water relative to the fluorinating agent.

As described above, Patent Document 15 (Japanese Unexamined Patent Publication No. 2002-234860) discloses a process for producing HFIP by decarboxylating the compound represented by general formula (3); with this process, however, even if decarboxylation is performed under acidic conditions, a large amount of the by-product, pentafluoroacetone represented by $HCF_2COCF_3$, is formed to decrease the yield. On the other hand, in the process of the invention, the pH of the reaction solution does not affect the yield of the target material, and, regardless of whether an acid is added or not, such a by-product in which the $CF_3$ group has been replaced with a $CF_2H$ group is not formed, thus resulting in decarboxylation at a high yield.

(ii) HF Addition Reaction of Olefin:

1,1,1,3,3,3-Hexafluoro-2-methoxypropane represented by chemical formula (2) can also be produced according to a process wherein 1,1,1,3,3,3-hexafluoro-2-methoxy-2-propene represented by chemical formula (4): $CF_2=C(CF_3)(OCH_3)$ (hereinafter referred to as an "olefin compound") is reacted with the above-described one or more fluorinating agents represented by the chemical formula: $MF \cdot (HF)_n$, wherein M is H, Na, K, or Cs, and n is an integer from 0 to 2.

As explained above, during the production of 1,1,1,3,3,3-hexafluoro-2-methoxypropane represented by general formula (2) via the decarboxylation reaction of the carboxylic acid represented by chemical formula (1): $(CF_3)_2C(OCH_3)$ COOH or its salt, an olefin compound of chemical formula (4): $CF_2=C(CF_3)(OCH_3)$ is formed as a by-product. When this olefin compound is reacted with one or more fluorinating agents represented by the chemical formula: $MF \cdot (HF)_n$, wherein M is H, Na, K, or Cs, and n is an integer from 0 to 2, the total yield of 1,1,1,3,3,3-hexafluoro-2-methoxypropane represented by general formula (2), based on the carboxylic acid represented by chemical formula (1) or its salt as a starting material, can be improved significantly.

The reaction between the olefin compound represented by chemical formula (4): $CF_2=C(CF_3)(OCH_3)$ and the fluorinating agent represented by the chemical formula: $MF \cdot (HF)_n$ can be performed using, for example, the above-mentioned organic solvent, water, or a mixed solvent of the above-mentioned organic solvent and water. The concentration of the olefin compound represented by chemical formula (4): $CF_2=C(CF_3)(OCH_3)$ in a solution may typically be from about 0.1 to about 8 mol/L. Especially when amide solvents such as N,N-dimethylformamide, N-methylpyrrolidone, N,N-dimethylacetamide, and the like; nitrile solvents such as acetonitrile, propionitrile, and the like; ketone solvents such as acetone, methyl ethyl ketone, methyl isobutyl ketone, and the like; sulfoxide solvents such as dimethyl sulfoxide and the like; or sulfone solvents such as sulfolane and the like are used as the organic solvent, the target 1,1,1,3,3,3-hexafluoroisopropyl ether compound represented by general formula (2) can be produced at high yield.

When the fluorinating agent is sodium fluoride, potassium fluoride, or cesium fluoride, the reaction must be performed in the presence of about an equimolar or excess amount of water relative to the fluorinating agent.

The amount of the fluorinating agent represented by the chemical formula: $MF \cdot (HF)_n$ is preferably from about 1 to about 2 equivalents per equivalent of the olefin compound represented by chemical formula (4): $CF_2=C(CF_3)(OCH_3)$.

The reaction between the olefin compound represented by chemical formula (4): $CF_2=C(CF_3)(OCH_3)$ and the fluorinating agent represented by the chemical formula: $MF \cdot (HF)_n$ can be typically performed within the range of temperatures from about 60 to about 120° C. While the reaction atmosphere at that time is not limited, the reaction is preferably performed in a sealed system with an inert gas atmosphere such as $N_2$ or the like.

While the reaction time depends upon the reaction temperature, the amount of additives, and the like, it is typically from about 1 to about 10 hours.

The 1,1,1,3,3,3-hexafluoro-2-methoxypropane of chemical formula (2) obtained by the above-described decarboxylation reaction or HF addition reaction can be separated and purified according to a known process. For example, purification can be performed according to processes such as distillation, extraction, etc.

Effects of the Invention

In accordance with the invention, 1,1,1,3,3,3-hexafluoro-2-methoxypropane, which is useful as an anesthetic compound or a raw material thereof, can be produced efficiently and at low cost, using a known hydroxycarboxylic ester represented by general formula (3) as a starting material.

Furthermore, in accordance with the invention, the novel carboxylic acid represented by chemical formula (1) or a salt thereof, which is useful as an intermediate or the like of 1,1,1,3,3,3-hexafluoro-2-methoxypropane, can be produced in a high yield.

BEST MODE FOR CARRYING OUT THE INVENTION

The present invention will be described in greater detail below with reference to Examples.

Example 1

(i) A 1 L four-necked flask equipped with a dropping funnel, a thermometer, and a stirrer was charged with 300 g (1.33 mol) of $(CF_3)_2C(OH)CO_2CH_3$ and 300 g of acetone, and 183 g (1.33 mol) of $K_2CO_3$ was added thereto while stirring the mixture in an ice bath. The ice bath was replaced with a water bath, and 176 g (1.39 mol) of $(CH_3O)_2SO_2$ was added dropwise in such a manner that the internal temperature was 30° C. or less. After an hour of stirring, the dropping funnel was replaced with a condenser tube, and the temperature was elevated to the reflux temperature to allow the reaction to proceed for 3 hours. Gas chromatographic analysis of the reaction product confirmed that $(CF_3)_2C(OH)CO_2CH_3$ had been completely consumed. H$_2$O was added, and the lower layer, i.e., the organic layer, was separated through a separating funnel, and then the organic layer was washed twice with H$_2$O. The resulting organic layer was distilled under reduced pressure (150 mmHg, 86-88° C.) to produce 247 g (1.03 mol) of (CF$_3$)$_2$C(OCH$_3$)CO$_2$CH$_3$ at an isolated yield of 78%.

(ii) Next, a 100 mL four-necked flask equipped with a dropping funnel, a condenser tube, a thermometer, and a stirrer was charged with 10 g (41.7 mmol) of (CF$_3$)$_2$C(OCH$_3$)CO$_2$CH$_3$, and then 8.34 g (41.7 mol) of 20 wt % aqueous NaOH solution was added dropwise while stirring at 60° C. After the dropwise addition was completed, the reaction was allowed to proceed at 60° C. for 3 hours. $^{19}$F NMR analysis of the reaction product confirmed that (CF$_3$)$_2$C(OCH$_3$)CO$_2$CH$_3$ had been completely consumed. The resulting reaction solution was evaporated to give 10.3 g of (CF$_3$)$_2$C(OCH$_3$)CO$_2$Na as a white solid. The spectral data of the resulting compound are as follows: $^{19}$F-NMR: −70.98 ppm (CF$_3$)

Example 2

A 100 mL four-necked flask equipped with a dropping funnel, a thermometer, and a stirrer was charged with 10 g (41.7 mmol) of (CF$_3$)$_2$C(OCH$_3$)CO$_2$CH$_3$ obtained in Step (i) of Example 1, and 11.7 g (41.7 mmol) of 20 wt % KOH was added dropwise while stirring in a water bath. After the dropwise addition was completed, the reaction was allowed to proceed for 18 hours in the water bath. $^{19}$F NMR analysis of the reaction product confirmed that (CF$_3$)$_2$C(OCH$_3$)CO$_2$CH$_3$ had been completely consumed. The resulting reaction solution was evaporated to give 11.0 g of (CF$_3$)$_2$C(OCH$_3$)CO$_2$K as a white solid. The spectral data of the resulting compound are as follows: $^{19}$F-NMR: −70.64 ppm (CF$_3$)

Example 3

A 100 mL four-necked flask equipped with a dropping funnel, a thermometer, and a stirrer was charged with 51.3 g (0.227 mol) of (CF$_3$)$_2$C(OH)CO$_2$CH$_3$, and 50 ml of water and 50 ml of ethanol were added, after which 51 g (0.227 mol) of 25% aqueous KOH solution was slowly added dropwise while heating and stirring the mixture in a warm bath at 40° C. The water layer was separated and concentrated with an evaporator to remove the methanol, to produce 79 g of aqueous (CF$_3$)$_2$C(OH)CO$_2$K solution.

Ten grams (0.029 mol) of the thus obtained aqueous potassium salt solution and 9.0 g (0.04 mol) of 25% aqueous KOH solution were added to a 100 ml four-necked flask, and then 5.0 g (0.04 mol) of dimethyl sulfate was slowly added dropwise at an internal temperature of 45° C. or less, while cooling with water and stirring. After the dropwise addition was completed, and after confirming that the internal temperature had stopped increasing, the mixture was heated in a warm bath and then heated and stirred for 3 hours at an internal temperature of 45 to 50° C. The results of analysis of the reaction solution showed that (CF$_3$)$_2$C(OCH$_3$)CO$_2$K was obtained at a conversion ratio of (CF$_3$)$_2$C(OH)CO$_2$K of 66% and at a selectivity of 100%.

$^{19}$F-NMR: −70.64 ppm (CF$_3$)

Example 4

An autoclave was charged with 2.0 g (3.0 mmol) of 1.5 mmol/g aqueous (CF$_3$)$_2$C(OCH$_3$)CO$_2$K solution prepared beforehand and 1.7 g of tetraethyleneglycol dimethyl ether (tetraglyme), and the reaction was allowed to proceed at 80° C. for 2 hours; as a result, the reaction pressure increased to 0.35 MPa from atmospheric pressure. After allowing the reaction product to cool, the residual pressure was released, and the resulting reaction product was analyzed by the $^{19}$F NMR internal standard method using trifluoroethanol. The results revealed that (CF$_3$)$_2$CH(OCH$_3$) was obtained at a conversion ratio of (CF$_3$)$_2$C(OCH$_3$)CO$_2$K of 99% or more and at a selectivity of 88%.

Example 5

An autoclave was charged with 2.0 g (3.0 mmol) of 1.5 mmol/g aqueous (CF$_3$)$_2$C(OCH$_3$)CO$_2$Na solution prepared beforehand, and 5 wt % aqueous H$_2$SO$_4$ solution was added thereto until the pH became 1. Then, 1.7 g of tetraethyleneglycol dimethyl ether (tetraglyme) was charged into the autoclave, and the reaction was allowed to proceed at 100° C. for 2 hours; as a result, the reaction pressure increased to 0.42 MPa from atmospheric pressure. After allowing the reaction product to cool, the residual pressure was released, and the resulting reaction product was analyzed by the $^{19}$F NMR internal standard method using trifluoroethanol. The results revealed that (CF$_3$)$_2$CH(OCH$_3$) was obtained at a conversion ratio of (CF$_3$)$_2$C(OCH$_3$)CO$_2$Na of 99% or more and at a selectivity of 90%.

Example 6

To a 10 mL autoclave was added 0.79 g (3.18 mmol) of (CF$_3$)$_2$C(OCH$_3$)CO$_2$Na, 0.86 ml (15 equivalents to the starting material) of water, and 4.14 ml each of the solvents shown in Table 1 below, and each mixture was heated and stirred at 150° C. for 3 hours. After cooling, a suitable amount of benzotrifluoride was added, and then the reaction yield was determined by $^{19}$F-NMR. The results are shown in Table 1 below.

In Table 1, the target (CF$_3$)$_2$CH(OCH$_3$) is denoted as "HFMOP"; the by-product CF$_2$=C(CF$_3$)(OCH$_3$) was denoted as an "olefin"; and CF$_3$CH(OCH$_3$)(COONa) was denoted as a "hydrolysis product". The solvents are each denoted by the following abbreviations: NMP (N-methylpyrrolidone), MeCN (acetonitrile), DMSO (dimethylsulfoxide), and DMAc (N,N-dimethylacetamide).

TABLE 1

| Type of Solvent | Reaction Yield (%) | | |
| --- | --- | --- | --- |
| | HFMOP | Hydrolysis Product | Olefin |
| NMP | 57 | 5.7 | 1 |
| MeCN | 53 | 0 | 8 |
| DMSO | 62 | 5 | Trace |
| DMAc | 45 | 4 | Trace |

Example 7

[Chemical Formula 1]

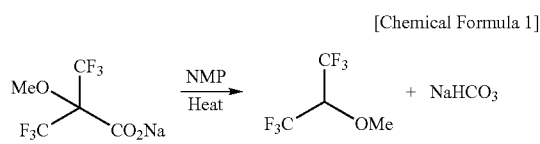

A 1 L SUS autoclave was charged with 150.5 g of 48.2 mass % aqueous (CF$_3$)$_2$C(OCH$_3$)CO$_2$Na solution (active compound amount: 292.5 mmol) and 300 ml of NMP solvent. The autoclave was subsequently sealed, and the decarboxylation reaction was performed at about 130° C. for 5.5 hours.

An ice bath trap and two dry-ice/acetone traps were connected to the reactor with a PFA tube. The pressure inside the autoclave was then released to the atmospheric pressure while stirring the contents.

When the internal pressure had dropped back to atmospheric pressure, the autoclave was heated stepwise to about 110° C. to extract the contents (until the water flowed out).

The solutions collected with the dry-ice/acetone traps and ice bath trap were mixed together, and then GC and NMR measurements were conducted to perform qualitative and quantitative analyses. The liquid (solvent) remaining in the autoclave was also subjected to NMR measurements to analyze the by-product. The results are shown in Table 2 below. In Table 2, each product is denoted by the same abbreviation as used in Table 1.

TABLE 2

| Charged Starting Material: 292.5 mmol | | | | |
|---|---|---|---|---|
| | HFMOP | Olefin | Hydrolysis Product | Total |
| Distillate | 223.1 mmol | 0.52 mmol | N.D. | 223.6 mmol |
| Still Residue | N.D. | N.D. | 30.0 mmol | 30.0 mmol |
| Total | 223.1 mmol | 0.52 mmol | 30.0 mmol | 253.6 mmol |

ND: Less than the analytical lower limit

The results shown above can be summarized as follows.
HFMOP yield: 223.1 mmol/292.5 mmol×100=76.3%
Distillate selectivity (HFMOP:olefin)=99.8%:0.2%
HFMOP:(olefin+hydrolysis product)=88.0%:12.0%
Material balance: 253.6 mmol/292.5 mmol×100=86.7%

Example 8

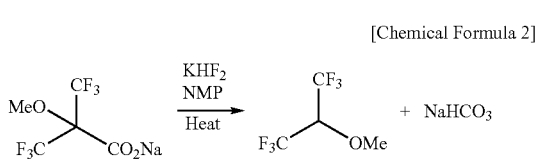

[Chemical Formula 2]

A 300 mL SUS autoclave was charged with 25.0 g (100.8 mmol) of $(CF_3)_2C(OCH_3)CO_2Na$, 11.4 g (146.2 mmol) of KF·HF, and 25 g of water to prepare about a 50 mass % aqueous solution. The pressure inside the autoclave was then reduced, and the autoclave was charged with 100 ml of NMP by suction. The decarboxylation reaction was subsequently performed at about 130 to about 150° C. for about 6 hours.

An ice bath trap and a dry-ice/acetone trap were connected to the reactor with a PFA tube. The pressure inside the autoclave was then released to the atmospheric pressure while stirring the contents.

When the internal pressure had dropped back to atmospheric pressure, the autoclave was heated stepwise to about 110° C. to extract the contents (until the water flowed out).

The solutions collected with the dry-ice/acetone trap and ice bath trap were mixed together, and then GC and NMR measurements were conducted to perform qualitative and quantitative analyses. The liquid (solvent) remaining in the autoclave was also subjected to NMR measurements to analyze the by-product. The results are shown in Table 3 below.

TABLE 3

| Charged Starting Material: 100.8 mmol | | | | |
|---|---|---|---|---|
| | HFMOP | Olefin | Hydrolysis Product | Total |
| Distillate | 92.6 mmol | N.D. | N.D. | 92.6 mmol |
| Still Residue | N.D. | N.D. | 0.88 mmol | 0.88 mmol |
| Total | 92.6 mmol | 0 | 0.88 mmol | 93.5 mmol |

ND: Less than the analytical lower limit

The results shown above can be summarized as follows.
HFMOP yield: 92.6 mmol/100.8 mmol×100=91.9%
Distillate selectivity (HFMOP:olefin)=99.9% up:N.D.
HFMOP:(olefin+hydrolysis product)=99.1%:0.9%
Material balance: 93.5 mmol/100.8 mmol×100=92.8%

Example 9

HF Addition Reaction of Olefin

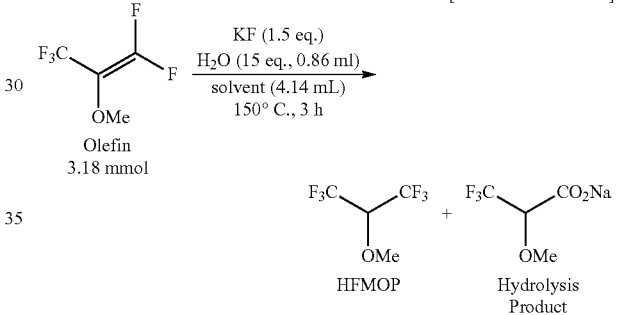

[Chemical Formula 3]

To a 10 mL autoclave was added 0.52 g (3.18 mmol) of $CF_3C(OCH_3)=CF_2$, 0.86 ml of water, 0.28 g (4.77 mmol) of potassium fluoride, and 4.14 ml each of the solvents shown in Table 4 below, and each mixture was heated and stirred at 150° C. for 3 hours. After cooling, a suitable amount of benzotrifluoride was added, and then the reaction yield was determined by $^{19}$F-NMR. The results are shown in Table 4 below.

In Table 4, each product is denoted by the same abbreviation as used in Table 1. In the column of solvents, the following abbreviations are used: NMP (N-methylpyrrolidone), MeCN (acetonitrile), DMSO (dimethyl sulfoxide), DMAc (N,N-dimethylacetamide), and DMF (dimethylformamide).

TABLE 4

| | Reaction Yield (%) | |
|---|---|---|
| Type of Solvent | HFMOP | Hydrolysis Product |
| NMP | 61 | 10 |
| MeCN | 43 | 14 |
| DMSO | 47 | 19 |
| Sulfolane | 49 | 4 |
| DMAc | 61 | 12 |
| DMF | 71[a] | — |

[a] Quantitatively measured by GC analysis.

Example 10

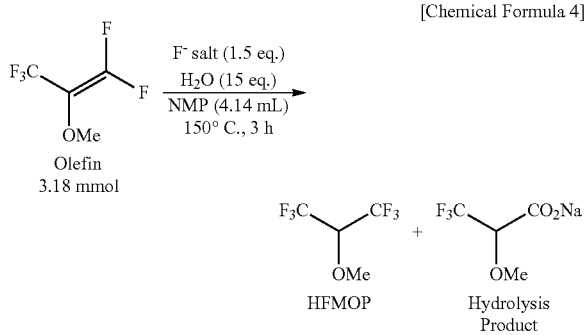

Olefin
3.18 mmol

To a 10 mL autoclave was added 0.52 g (3.18 mmol) of $CF_3C(OCH_3)=CF_2$, 0.86 ml of water, 4.14 ml of NMP, and 1.5 equivalents of each of the fluorinating agents shown in Table 5 below per equivalent of $CF_3C(OCH_3)=CF_2$, and then each mixture was heated and stirred at 150° C. for 3 hours. After cooling, a suitable amount of benzotrifluoride was added, and then the reaction yield was determined by $^{19}$F-NMR. The results are shown in Table 5 below.

TABLE 5

| Type of Fluorinating Agent (F⁻ Salt) | Reaction Yield (%) | |
|---|---|---|
| | HFMOP | Hydrolysis Product |
| KHF$_2$ | 67 | 4 |
| NaF | 58 | 1 |
| CsF | 60 | 11 |
| KF | 71 | 11 |

The invention claimed is:

1. 2-Methoxy-2-trifluoromethyl-3,3,3-trifluoropropionic acid represented by chemical formula (1): $(CF_3)_2C(OCH_3)COOH$ or a salt thereof.

2. A process for producing 1,1,1,3,3,3-hexafluoro-2-methoxypropane represented by chemical formula (2): $(CF_3)_2CH(OCH_3)$, comprising decarboxylating 2-methoxy-2-trifluoromethyl-3,3,3-trifluoropropionic acid represented by chemical formula (1): $(CF_3)_2C(OCH_3)COOH$ or a salt thereof.

3. The process for producing 1,1,1,3,3,3-hexafluoro-2-methoxypropane according to claim 2, wherein the decarboxylation reaction is performed in the presence of an organic solvent.

4. The process for producing 1,1,1,3,3,3-hexafluoro-2-methoxypropane according to claim 2, wherein the decarboxylation reaction is performed in the presence of an organic solvent and an equimolar or excess amount of water relative to the 2-methoxy-2-trifluoromethyl-3,3,3-trifluoropropionic acid represented by chemical formula (1): $(CF_3)_2C(OCH_3)COOH$ or a salt thereof.

5. The process for producing 1,1,1,3,3,3-hexafluoro-2-methoxypropane according to claim 4, wherein the organic solvent is at least one solvent selected from the group consisting of amide solvents, nitrile solvents, ketone solvents, sulfone solvents, and sulfoxide solvents.

6. The process for producing 1,1,1,3,3,3-hexafluoro-2-methoxypropane according to claim 5, wherein the decarboxylation reaction is performed further in the presence of one or more fluorinating agents represented by the chemical formula: $MF.(HF)_n$, wherein M is H, Na, K, or Cs, and n is an integer from 0 to 2.

7. A process for producing 1,1,1,3,3,3-hexafluoro-2-methoxypropane represented by chemical formula (2): $(CF_3)_2CH(OCH_3)$, comprising reacting 1,1,1,3,3,3-hexafluoro-2-methoxy-2-propene represented by chemical formula (4): $CF_2=C(CF_3)(OCH_3)$ with one or more fluorinating agents represented by the chemical formula: $MF.(HF)_n$, wherein M is H, Na, K, or Cs, and n is an integer from 0 to 2.

8. A process for producing 2-methoxy-2-trifluoromethyl-3,3,3-trifluoropropionic acid represented by chemical formula (1): $(CF_3)_2C(OCH_3)COOH$ or a salt thereof, comprising reacting a methylating agent with a hydroxycarboxylic ester represented by general formula (3):

$(CF_3)_2C(OH)COOR$, wherein R is a hydrocarbon group, and may contain at least one atom selected from the group consisting of halogen, oxygen, nitrogen, and sulfur atoms, and subsequently hydrolyzing the resulting reaction product.

9. The process according to claim 8, wherein the methylating agent is at least one compound selected from the group consisting of dimethyl sulfate, chloromethane, bromomethane, and iodomethane.

10. A process for producing 2-methoxy-2-trifluoromethyl-3,3,3-trifluoropropionic acid represented by chemical formula (1): $(CF_3)_2C(OCH_3)COOH$ or a salt thereof, comprising hydrolyzing a hydroxycarboxylic ester represented by general formula (3):

$(CF_3)_2C(OH)COOR$, wherein R is a hydrocarbon group, and may contain at least one atom selected from the group consisting of halogen, oxygen, nitrogen, and sulfur atoms, to produce 1,1,1-trifluoro-2-trifluoromethyl-2-hydroxypropionic acid represented by the chemical formula: $(CF_3)_2C(OH)CO_2H$ or a salt thereof, and subsequently reacting the resulting product with a methylating agent.

11. The process according to claim 10, wherein the methylating agent is at least one compound selected from the group consisting of dimethyl sulfate, chloromethane, bromomethane, and iodomethane.

12. The process for producing 1,1,1,3,3,3-hexafluoro-2-methoxypropane according to claim 3, wherein the organic solvent is at least one solvent selected from the group consisting of amide solvents, nitrile solvents, ketone solvents, sulfone solvents, and sulfoxide solvents.

13. The process for producing 1,1,1,3,3,3-hexafluoro-2-methoxypropane according to claim 12, wherein the decarboxylation reaction is performed further in the presence of one or more fluorinating agents represented by the chemical formula: $MF.(HF)_n$, wherein M is H, Na, K, or Cs, and n is an integer from 0 to 2.

14. The process for producing 1,1,1,3,3,3-hexafluoro-2-methoxypropane according to claim 2, wherein the decarboxylation reaction is performed further in the presence of one or more fluorinating agents represented by the chemical formula: $MF.(HF)_n$, wherein M is H, Na, K, or Cs, and n is an integer from 0 to 2.

15. The process for producing 1,1,1,3,3,3-hexafluoro-2-methoxypropane according to claim 3, wherein the decarboxylation reaction is performed further in the presence of one or more fluorinating agents represented by the chemical formula: $MF.(HF)_n$, wherein M is H, Na, K, or Cs, and n is an integer from 0 to 2.

* * * * *